(12) United States Patent
Bouali et al.

(10) Patent No.: US 6,423,700 B1
(45) Date of Patent: Jul. 23, 2002

(54) 17-HALOGENATED 19-NOR STEROIDS, METHOD AND INTERMEDIATES FOR PREPARING SAME, USE AS MEDICINES AND PHARMACEUTICAL COMPOSITIONS CONTAINING SAME

(75) Inventors: Yasmina Bouali, Villejuif; Jacques Mauger; Patrick Van De Velde, both of Paris; Francois Nique, Le Perreux sur Marne, all of (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/720,565

(22) PCT Filed: Jun. 22, 1999

(86) PCT No.: PCT/FR99/01491

§ 371 (c)(1),
(2), (4) Date: Jan. 5, 2001

(87) PCT Pub. No.: WO99/67274

PCT Pub. Date: Dec. 29, 1999

(30) Foreign Application Priority Data

Jun. 23, 1998 (FR) .............................. 98 07898

(51) Int. Cl.$^7$ .................. A61K 31/58; A61K 31/56; C07J 1/00; C07J 43/00
(52) U.S. Cl. .................. 514/176; 514/182; 540/107; 540/108; 540/113; 552/618
(58) Field of Search ................ 514/176, 182; 540/107, 108, 113; 552/502, 618

(56) References Cited

U.S. PATENT DOCUMENTS

| 3,079,408 A | 2/1963 | Mueller |
| 3,275,623 A | 9/1966 | Knox |
| 3,413,321 A | 11/1968 | Boswell |

FOREIGN PATENT DOCUMENTS

| FR | 2640977 | 6/1990 |
| WO | 9828324 | 7/1998 |
| WO | 9845316 | 10/1998 |
| WO | 9925725 | 5/1999 |

OTHER PUBLICATIONS

Jin et al, "Antiestrogenic . . . Cancer Cells", Steroids: Structure, Function, and Regulation, vol. 60, No. 8, Aug. 1995, pp. 512–518.
Brunner et al, "Synthese . . . Ostradiolderivaten", Monatshefte fur Chemie, vol. 124, No. 1, 1993, pp. 82–102.
Arunachalam et al, "Iodoestrogens, . . . Receptors", Journal of Biological Chemistry, vol. 254, No. 13, Jul. 10, 1979, pp. 5900–5905.

*Primary Examiner*—Barbara P. Badio
(74) *Attorney, Agent, or Firm*—Bierman, Muserlian and Lucas

(57) ABSTRACT

A compound of the formula wherein the substituents are as defined in the application and its non-toxic, pharmaceutically acceptable acid and base salts useful for hormone replacement for treating menopause or perimenopause without activity at the uterine level treating osteoporosis and strengthening cardiovascular protection in warm-blooded animals.

10 Claims, No Drawings

17-HALOGENATED 19-NOR STEROIDS, METHOD AND INTERMEDIATES FOR PREPARING SAME, USE AS MEDICINES AND PHARMACEUTICAL COMPOSITIONS CONTAINING SAME

This application is a 371 of PCT/FR99/01491 filed on Jun. 22, 1999.

The present invention relates to 17-halogenated 19-nor steroid compounds, their preparation process and intermediates, their use as a medicament and the pharmaceutical compositions containing them.

Osteoporosis is a pathology which is characterized by a quantitative and qualitative reduction in bone matter, sufficient to lead to vertebral or peripheral fractures, in a spontaneous fashion or on occasions due to minimal traumas. Although this illness has many factors at its origin, it is the menopause which in women constitutes the dominating factor in bone loss or osteopenia.

This osteopenia manifests itself by a rarefaction and modification of the architecture of the spongy bone, the consequence of which is to increase the fragility of the skeleton and the risk of fractures. Bone loss increases strongly after the menopause due to the suppression of ovarian function and reaches 3 to 5% per year before slowing down after 65 years old.

For a therapeutic purpose, the post-menopause hormonal deficiency can be compensated for by a hormone replacement therapy where oestrogen plays a major role in preserving the bone mass. But long-term oestrogenotherapy is sometimes accompanied by undesirable effects on the genital apparatus (endometrial hyperplasia, breast tumors . . . ), which constitutes a major drawback and limits its use.

It is therefore convenient to find compounds other than oestradiol having a dissociated oestrogen activity, namely an oestrogen activity at the bone level, while having no or little endometrial hyperplasia activity, nor breast tumor proliferation activity.

Therefore, a subject of the invention is the compounds of general formula (I):

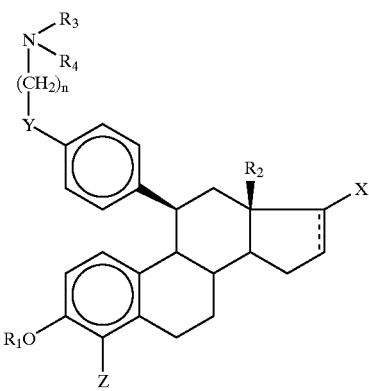

in which:
$R_1$ represents a hydrogen atom, a $(CH_2)_m$—Ar, (CO)—Ar, $(CH_2)_m$—Alk or (CO)—Alk radical,
$R_2$ represents a radical derived from a linear or branched, saturated or unsaturated hydrocarbon containing 1 to 6 carbon atoms
X represents a halogen atom,
Y represents a single bond, O, NH, S, SO or $SO_2$,
Z represents a hydrogen atom or a halogen atom,
n is equal to 2, 3, 4 or 5,
either $R_3$ and $R_4$ identical or different, represent a hydrogen atom, a $(CH_2)_{m'}$—Ar, $(CH_2)_{m'}$—Het or $(CH_2)_{m'}$Alk group,
or $R_3$ and $R_4$ form together with the nitrogen atom to which they are linked an aromatic or non-aromatic, saturated or unsaturated mono- or polycyclic heterocycle with 3 to 15 members optionally containing 1 to 3 additional heteroatoms chosen from oxygen, sulphur and nitrogen, non-substituted or substituted,
Ar representing a carbocyclic aryl group containing 6 to 18 carbon atoms, Het representing a saturated or unsaturated aromatic or non-aromatic heterocycle containing 1 to 9 carbon atoms and 1 to 5 heteroatoms chosen from oxygen, nitrogen or sulphur atoms, Alk representing a radical derived from a saturated or unsaturated, linear, branched or cyclic, non-aromatic hydrocarbon and containing 1 to 12 carbon atoms, the Ar, Het or Alk radicals being able to be substituted or non-substituted, m and m' representing 0, 1, 2 or 3, the dotted lines representing an optional second bond, as well as their addition salts with bases or acids.

By halogen is meant: iodine, bromine, chlorine or fluorine. In position 4, it is preferably chlorine or bromine. In position 17, it is preferably fluorine.

By $(CH_2)_m$ or $(CH_2)_{m'}$ is meant the following values: single bond in the case where m is equal to 0, $CH_2$, $(CH_2)_2$ and $(CH_2)_3$.

By the term Ar representing the carbocyclic aryl group containing 6 to 18 carbon atoms is meant a derivative of an aromatic cyclic hydrocarbon such as the phenyl, naphthyl, phenanthrenyl radical or a derivative of a condensed, bicyclic or tricyclic hydrocarbon containing a benzene ring such as indanyl, indenyl, dihydronaphthyl, tetrahydronaphthyl or fluorenyl. The junction is carried out at the level of the benzene ring. Preferably it is phenyl.

By the term (Het) representing a saturated or unsaturated, aromatic or non aromatic heterocycle containing 1 to 9 carbon atoms and 1 to 5 heteroatoms chosen from oxygen, nitrogen and sulphur atoms, the following are designated in particular:
heterocyclic monocyclic radicals, for example thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl, imidazolinyl, pyrazolinyl, thiazolinyl, triazolyl, tetrazolyl radicals,
condensed heterocyclic rings, for example benzofuranyl, benzothienyl, benzimidazolyl, benzothiazolyl, naphtho[2, 3-b] thienyl, thianthrenyl, isobenzofuranyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl or also condensed polycyclic systems constituted by heterocyclic moncyclics as defined above such as for example furo[2,3-b] pyrrole or thieno[2,3-b] furan,
or saturated heterocycles such as pyrrolidine, piperidine, morpholine.

By the term (Alk) representing a radical derived from a saturated, linear, branched or cyclic non-aromatic hydrocarbon, is designated in the case of acyclic hydrocarbons the alkyl radicals such as methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethyl pentyl, 3-ethylpentyl, n-octyl, 2,2-dimethylhexyl, 3,3-dimethylhexyl, 3-methyl-3-ethylpentyl, nonyl, 2,4-dimethylheptyl or n-decyl, the alkenyl radicals such as vinyl, propenyl, isopropenyl, allyl, 2-methylallyl, butenyl or isobutenyl, or the alkynyl radicals such as ethynyl, propynyl, propargyl, butynyl or isobutynyl, and in the case of cyclic radicals, the cycloalkyl radicals, such as cyclopropyl, cyclobutyl, cyclopentyl, cyclohexyl or adamantyl.

It will preferably be methyl and ethyl radicals. By CO—Alk is preferably meant COCH$_3$ and COEt, by CO—Ar is preferably meant the benzoyl radical, when m is different from zero, (CH$_2$)$_m$—Ar will preferably be the benzyl group.

When R$_3$ and R$_4$ form together with the nitrogen atom to which they are linked a heterocycle, it is in particular mono- or bicyclic heterocycles optionally containing another heteroatom chosen from oxygen and nitrogen such as the following unsaturated heterocycles: pyrrolyl, imidazolyl, indolyl, pyridyl, pyrazinyl, pyrimidinyl, pyridazinyl, thiazolyl, oxazolyl, furazolinyl, pyrazolinyl, thiazolinyl, or, more particularly, the following saturated heterocycles:

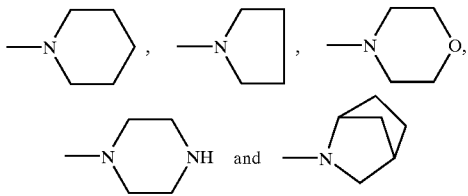

When the different Alk, Ar, Het groups, as well as the heterocycle formed by R$_3$ and R$_4$ with the nitrogen which carries them, are substituted, they can in particular be substituted by the following radicals:
halogen, namely fluorine, chlorine, bromine or iodine, alkoxy such as methoxy, ethoxy, propyloxy, isopropyloxy, butyloxy, alkylthio such as methylthio, ethylthio, propylthio, isopropylthio, butylthio, amino, alkylamino such as methylamino or ethylamino, dialkylamino such as dimethylamino, diethylamino, methylethylamino, each of these dialkylamino radicals being optionally in oxidized form, aminoalkyl such as aminomethyl or aminoethyl, dialkylaminoalkyl such as dimethylamino methyl or ethyl, dialkylaminoalkyloxy such as dimethylamino ethyloxy, hydroxyl optionally acylated, acyl such as acetyl, propionyl, butyryl, benzoyl, free, esterified carboxy such as alkoxy carbonyl for example methoxy carbonyl or ethoxy carbonyl, cyano, trifluoromethyl, aryl such as phenyl, aralkyl such as benzyl, alkyl, alkenyl or alkynyl these radicals being themselves optionally substituted by the halogen, alkyl, alkoxy, alkylthio, amino, alkylamino or dialkylamino radicals indicated above.

Of course, the expression "substituted" indicates that one or more identical or different substituents can be present. By way of example, when the alkyl group is a methyl radical substituted by one or more halogen atoms, it can in particular be CH$_2$Cl, CH$_2$F, CHF$_2$ and CF$_3$. In the case of (Het), the substituents can be at the level of NH or a carbon atom.

Of course the values of R$_1$, R$_2$, R$_3$ and R$_4$, as well as n, m and m' are independent of each other.

The invention naturally extends to the salts of the compounds of formula (I), such as for example the salts formed with mineral or organic acids on the amine. It can then be one of the following acids: hydrochloric, hydrobromic, nitric, sulphuric, phosphoric, acetic, formic, propionic, benzoic, maleic, fumaric, succinic, tartaric, citric, oxalic, glyoxylic, aspartic, alkane sulphonics such as methane or ethane sulphonic acids, arylsulphonics, such as benzene or paratoluene sulphonic acids and arylcarboxylics. When the compounds of formula (I) contain an acid function, the invention extends to the salts of alkali metals, alkaline earth metals or ammonium, optionally substituted.

A more particular subject of the invention is the compounds of general formula (I) as defined above as well as their addition salts, in which X is a fluorine atom in the alpha position, and the dotted lines do not represent a second bond (ring D of the saturated steroid).

Also a more particular subject of the invention is the compounds of general formula (I) as defined previously as well as their addition salts, in which R$_1$ is a hydrogen atom, R$_2$ is a methyl radical and Z is either a hydrogen atom or a chlorine atom, Y represents an oxygen atom and the dotted lines do not represent a second bond.

A quite particular subject of the invention is the compounds of general formula (I) as defined previously as well as their addition salts, in which:
either R$_3$ and R$_4$, identical or different, represent an alkyl radical containing 1 to 6 carbon atoms,
or R$_3$ and R$_4$ together with the nitrogen atom to which they are linked, form one of the following saturated heterocycles:

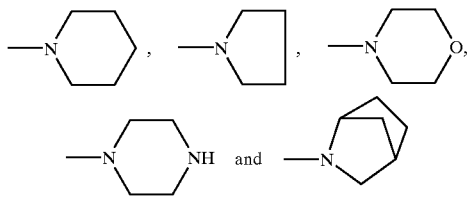

Also a quite particular subject of the invention is the compounds of general formula (I) as defined previously as well as their addition salts, in which X is a fluorine atom in alpha position, R$_1$ is a hydrogen atom, R$_2$ is a methyl radical, Y is an oxygen atom, Z is a hydrogen atom or chlorine atom, n is equal to 2 or 3,
either R$_3$ and R$_4$, identical or different, represent an alkyl radical containing 1 to 6 carbon atoms,
or R$_3$ and R$_4$ together with the nitrogen atom to which they are linked, form one of the following saturated heterocycles:

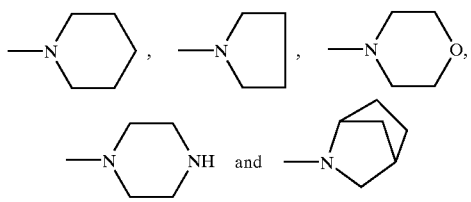

and the dotted lines do not represent a second bond.

Finally a subject of the invention is the compounds of formula (I) as well as their addition salts with acids the names of which follow:
17-alpha-fluoro-11-beta-[4-[2-(1-piperidinyl)ethoxy] phenyl]-estra-1,3,5(10)-trien-3-ol
17-alpha-fluoro-11-beta-[4-[2-(1-piperidinyl)ethoxy] phenyl]-estra-1,3,5(10)-trien-3-ol hydrochloride
17-alpha-fluoro-11-beta-[4-[2-(1-diethylamino)ethoxy] phenyl]-estra-1,3,5(10)-trien-3-ol
17-alpha-fluoro-11-beta-[4-[2-(1-pyrrolidinyl)ethoxy] phenyl]-estra-1,3,5(10)-trien-3-ol 4-chloro-17-alpha-fluoro-11-beta-[4-[2-(1-piperidinyl)
ethoxy]phenyl]-estra-1,3,5(10)-trien-3-ol
17-iodo-11-beta-[4-[2-(1-piperidinyl)ethoxy]phenyl]-estra-
1,3,5(10),16-tetraen-3-ol,
17-alpha-fluoro-11-beta-[4-[2-(4-methyl-1-piperidinyl)
ethoxy]-phenyl]-estra-1,3,5(10)-trien-3-ol,
17-alpha-fluoro-11-beta-[4-[2-(4-methyl-1-piperidinyl)
ethoxy]-phenyl]-estra-1,3,5(10)-trien-3-ol hydrochloride,
17-alpha-fluoro-3-methoxy-11-beta-[4-[2-(1-piperidinyl)
ethoxy]-phenyl]-estra-1,3,5(10)-triene,
17-alpha-fluoro-3-methoxy-11-beta-[4-[2-(1-pyrrolidinyl)
ethoxy]-phenyl]-estra-1,3,5(10)-triene,
17-alpha-fluoro-3-methoxy-11-beta-[4-[2-(diethylamino)
ethoxy]-phenyl]-estra-1,3,5(10)-triene,
(11-beta)-17-chloro-11-[4-[2-(1-piperidinyl)ethoxy]-
phenyl]-estra-1,3,5(10),16-tetraen-3-ol,
17-alpha-chloro-11-beta-[4-[2-(1-piperidinyl)ethoxy]-
phenyl]-estra-1,3,5(10)-trien-3-ol,
17-iodo-11-beta-[4-[2-(1-piperidinyl)ethoxy]-phenyl]-estra-
1,3,5(10),16-tetraen-3-ol hydrochloride,
17-alpha-fluoro-11-beta-[4-[2-(1-piperidinyl)ethoxy]-
phenyl]-estra-1,3,5(10)-trien-3-ol lactate.

A subject of the invention is also a preparation process for the compounds of formula (I) as defined previously, in which a compound of formula (II)

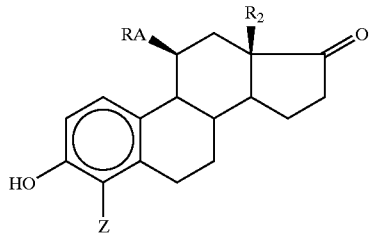

(II)

in which $R_2$ and Z are as defined previously,

RA represents one of the following groups:

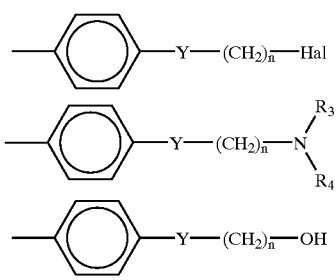

in which Y, n, $R_3$ and $R_4$ are as defined previously and Hal represents a halogen atom, is subjected to the action, if appropriate after protection and/or activation of the OH functions, either a) of a reducing agent of the keto in position 17 in order to obtain a compound of formula (III$_a$)

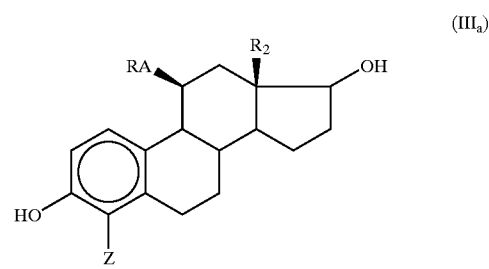

(III$_a$)

b) then of a halogenation agent in order to obtain a compound of formula (I'$_a$):

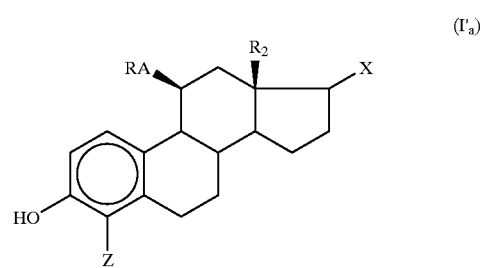

(I'$_a$)

corresponding to certain compounds of formula (I), when RA represents —Ph—Y—(CH$_2$)$_n$—NR$_3$R$_4$, or a) of a hydrazine in order to obtain a compound of formula (III$_b$):

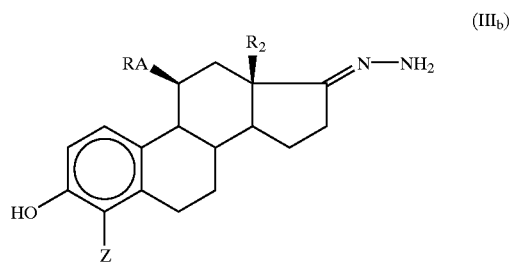

(III$_b$)

b) then of a halogenation agent in order to obtain a compound of formula (I'$_b$):

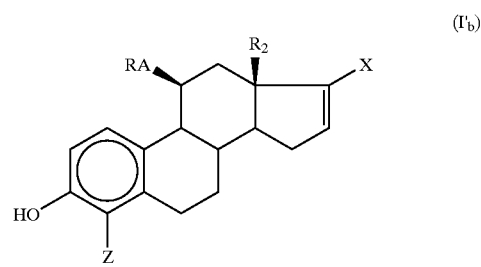

(I'$_b$)

corresponding to certain compounds of formula (I), when RA represents —Ph—Y—(CH$_2$)$_n$—NR$_3$R$_4$, the compounds of formula (II), (III$_a$), (III$_b$), (I'$_a$) or (I'$_b$), in protected or unprotected form, being subjected, if desired or if necessary, to one or more of the following reactions:
deprotection of the protected OH group or groups,
acylation/alkylation of the OH group or groups,
the action of HNR$_3$R$_4$, optionally in the form of a salt, when RA represents the —Ph—Y—(CH$_2$)$_n$—Hal or activated —Ph—Y—(CH$_2$)$_n$—OH group,
salification.

The reduction of 17-keto into the alcohol is carried out according to standard methods, in particular by the action of an alkaline borohydride such as sodium borohydride in methanol or ethanol or by the action of aluminium and lithium tetrahydride.

This reduction allows in particular the alcohol in position 17-beta to be obtained.

The halogenation reaction which follows is preferably carried out with reagents such as $XSO_2C_4F_9$ in the presence of a hindered base such as DBU (diazabicycloundecene), X is preferably fluorine. Other halogenation methods known to a person skilled in the art can also be used.

When the hydroxy group of the starting product is in the beta position, an inversion of the configuration is observed during the nucleophilic substitution and by this process (halogenation reagent: perfluoro-1-butane sulphonyl fluoride ($FSO_2C_4F_9$)) quite particularly the compounds of formula (I) or (I'$_a$) are obtained with the fluorine in the 17-alpha position.

The action of hydrazine is preferably carried out in the presence of a base such as triethylamine and the halogenation which follows is carried out in particular with $X_2$ in a basic medium and in particular with $I_2$.

By activation of the alcohol is meant the introduction in particular of a mesylate, tosylate or triflate which encourages the nucleophilic substitution of the amine $HNR_3R_4$ on the compounds of formulae (II), (III$_a$), (III$_b$), (I'$_a$), (I'$_b$) in which $R_3$ represents a —Ph—Y—(CH$_2$)$_n$—OH group.

The formation of the mesylate, tosylate or triflate from the corresponding alcohol is carried out in the presence of a base such as triethylamine. The substitution of the alcohol by a halogen atom according to the usual methods can also be envisaged beforehand.

The protection and deprotection reactions are standard methods known to a person skilled in the art. A fairly complete review is contained in the following publication: Protective groups in organic synthesis, T. W. Greene, John Wiley & sons (1981).

The protective group P (OH→OP) can represent an alkyl radical containing 1 to 4 carbon atoms, a benzyl group, a tetrahydropyrannyl group, an R$_C$R$_D$R$_E$Si group in which R$_C$, R$_D$ and R$_E$ identical or different, independent of one another, each represent an alkyl radical containing 1 to 4 carbon atoms or a phenyl group. This is quite particularly the Si(Me)$_2$CMe$_3$ or —Si(Ph)$_2$CMe$_3$ or —SiMe$_3$ groups.

As an example, the deprotection reactions (OP→OH in position 3), when P is a tertbutyldiphenylsilyl group can be carried out by the action of tetrabutyl ammonium fluoride in solution in tetrahydrofuran. It is the same when P represents SO$_2$C$_4$F$_9$ following the fluoridation reaction.

When P is a tetrahydropyrannyl group, the deprotection is carried out in the presence of an aqueous acid in an alcoholic solvent and preferably by the action of hydrochloric acid in methanol.

The action of a compound of formula R$_3$R$_4$NH on the compounds of formulae (II), (III$_a$), (III$_b$), (I'$_a$), (I'$_b$) in which R$_2$ represents a —Ph—Y—(CH$_2$)$_n$—OH or —Ph—Y—(CH$_2$)$_n$—Hal group is carried out under standard conditions for nucleophilic substitutions, in particular in the presence of an aprotic solvent such as tetrahydrofuran. When OH is activated it is in particular OSO$_2$CH$_3$, OSO$_2$—Ph—pMe, OSO$_2$CPh$_3$.

The alkylation or acylation reactions of the OH group in position 3 as well as the salification reactions are carried out by the standard methods known to a person skilled in the art.

The compounds of general formula (I) as well as their addition salts with pharmaceutically acceptable acids have in particular oestrogen, anti-oestrogen and anti-proliferative activities.

Therefore the compounds of formula (I) can be used in the treatment of disorders linked to hypofolliculinia, for example, amenorrheas, dysmenorrheas, repeated abortions, premenstrual disorders, in the treatment of certain oestrogen-dependent pathologies such as prostatic adenomas or carcinomas, mammary carcinomas and their metastases or in the treatment of benign breast tumors, as an anti-uterotrophic as well as in the replacement treatment for the menopause or the perimenopause.

Among the symptoms and consequences linked to the menopause are more specifically meant hot flushes, sweats, vaginal atrophy and dryness, urinary symptoms and in the long term a reduction in bone mass and an increased risk of fractures, and the loss of the cardiovascular protection provided by oestrogens.

In particular, the compounds of formula (I) as well as their addition salts with pharmaceutically acceptable acids or bases can be used in the prevention or the treatment of osteoporosis.

The compounds of formula (I) and their addition salts with pharmaceutically acceptable acids or bases can also be used for the prevention or the treatment of osteoporosis in man.

They can also be used for the prevention or the treatment of secondary osteoporoses (for example cortisonal or linked with immobilization).

The compounds of formula (I) as well as their addition salts with pharmaceutically acceptable acids or bases in particular have a dissociated oestrogenic activity.

By dissociated oestrogenic activity is meant an oestrogenic activity at bone level while demonstrating only minimal activity at uterine level, thus not entailing an endometrial proliferation (much lower activity than that of oestradiol).

Furthermore, the compounds according to the invention have the following advantages:

They have an anti-oestrogenic and/or anti-proliferative activity at the level of the breast. Unlike oestradiol, they do not stimulate the growth of human mammary tumor cells and can even inhibit their growth. The compounds according to the invention are therefore particularly advantageous for the treatment of the menopause in women at risk from breast cancer (family antecedents) who are therefore excluded from a replacement treatment using oestradiol.

They can also be used in the treatment of breast cancers.

They lead to a lowering of the seric cholesterol level to a level equivalent to that induced by oestradiol. Therefore, they strengthen cardiovascular protection.

Finally, as the compounds according to the invention have no oestrogen activity at the uterine level, they do not require to be administered in combination with a progestomimetic compound.

A subject of the invention is thus compounds of formula (I) as well as their addition salts with pharmaceutically acceptable acids or bases, as medicaments.

A more particular subject of the invention is compounds of formula (I) as well as their addition salts with pharmaceutically acceptable acids or bases as medicaments intended for the prevention or the treatment of osteoporosis.

The invention extends to the pharmaceutical compositions containing at least one of the medicaments defined above as active ingredient.

The compounds of formula (I) are used by digestive, parenteral or local route, for example by percutaneous route. They may be prescribed in the form of plain or coated tablets, gelatin capsules, granules, suppositories, pessaries, injectable preparations, ointments, creams, gels, microspheres, implants, intravaginal rings, patches, which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The useful dose varies as a function of the illness to be treated and the administration route; it can vary for example from 1 to 1000 mg per day for an adult by oral route.

A subject of the invention is also the use of compounds of formula (I) as defined above, for the preparation of a medicament intended for hormone replacement treatment for the menopause or the perimenopause, having little or no activity at the uterine level, and quite particularly the use, characterized in that the medicament is intended for the prevention or treatment of osteoporosis.

The compounds of formula (II) or(III$_a$) are compounds which are known or are easily accessible to a person skilled in the art. In particular, the compounds of formula (II) with Z=H, R$_2$=Me and RA=—Ph—Y—(CH$_2$)$_n$—Hal are described in the International Application WO 93/13123 (compounds of formula II); the compounds of formula (II) with Z=H, R$_2$=Me and RA=—Ph—Y—(CH$_2$)$_n$—OH are described in the European Patent 0305242 B1 (compounds of formula (III)), the compounds of formula (II) with Z=H, R$_2$=Me and RA=—Ph—Y—(CH$_2$)$_n$—NR$_3$R$_4$ are described in European Patent 0097572, the French Addition Certificate 2640977 or the European Patent 0305242.

The compounds of formula (II) in which Z represents a halogen atom are described in the International Application Wo 9845316 and are prepared from the compound of formula (IV):

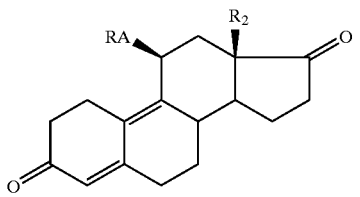

(IV)

by the action of a halogenation reagent in order to obtain the compound of formula (V):

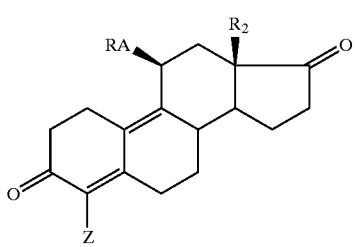

(V)

which compound (V) is subjected to the action of an aromatization reagent of ring A, then to the action of a base in order to obtain the compound of formula (II) in which Z represents a halogen atom.

The action of a halogenation reagent such as N-bromosuccinimide or N-chloromosuccinimide on the compounds of formula (IV) is carried out in particular in the presence of a dipolar aprotic solvent such as dimethylformamide.

The aromatization reaction followed by the saponification reaction (action of the base) is carried out according to standard methods as described in the European Patent 0097572. Preferably an acetic anhydride and acetyl bromide mixture is used as aromatization agent then a base such as soda in methanol is used as saponification agent.

A subject of the invention is also, as intermediate products, the compounds of formulae (I'$_a$), (III$_b$) and (I'$_b$).

The examples below illustrate the invention without however limiting it.

Solvents described in the examples: AcOEt (ethyl acetate), TEA (triethylamine), CH$_2$Cl$_2$ (dichloromethane), CHCl$_3$ (chloroform), MeOH (methanol), NH$_4$OH (ammonium hydroxide), iPrOH (isopropyl alcohol).

EXAMPLE 1

17 alpha-fluoro-11 beta-[4-[2-(1-piperidinyl)ethoxy]phenyl]-estra-1,3,5(10)-trien-3-ol Stage A: Reduction 11 beta-[4-(2-iodoethoxy)phenyl]estra-1,3,5(10)-triene-3,17 beta-diol 76 mg of sodium borohydride is added to a solution at 0° C. of 516 mg of 3-hydroxy-11 beta-[4-(2-iodoethoxy)phenyl]estra-1,3,5(10)-trien-17-one prepared according to the method described in WO 93/13123 in 5 ml of MeOH and 5 ml of THF, and agitation is carried out at this temperature for 5 minutes then for 1 hour 30 minutes at ambient temperature. 20 ml of 0.1N HCl is then added and crystallization is observed. 460 mg of expected product is obtained.

Rf AcOEt/TEA 95/5=0.67

NMR (CDCl$_3$, 300 MHz) 7.01 and 6.61 (4H, 2d, aromatic H in position 11); 6.79 (1H, d, H1); 6.68 (1H, d, H4); 6.51 (1H, dd, H2); 4.11 (2H, t, CH$_2$O); 3.94 (1H, bt, H11)); 3.72 (1H, bt, H17); 3.33 (2H, t, CH$_2$I) ; 0.37 (3H, s, 18-Me)

Stage B: Fluoridation 17 alpha-fluoro 11-beta-[4-(2-iodoethoxy)phenyl]-estra-1,3,5(10)-trien-3-ol nonafluorobutanesulphonate.

0.45 ml of DBU then 0.20 ml perfluoro-1-butane sulphonyl fluoride (FSO$_2$C$_4$F$_9$) is added at 0° C. and under nitrogen to a suspension of 518 mg of the steroid prepared in Stage A in 5 ml of toluene and 1 ml of dichloromethane, and the solution obtained is maintained at ambient temperature for 30 minutes. The reaction medium is then poured into 20 ml of water, extracted with ethyl acetate, washed, dried and evaporated under reduced pressure in order to obtain 565 mg of crude product which is purified by chromatography on Lichrosorb RP18, eluting with an acetonitrile/water mixture 85/15. 350 mg of expected product is obtained.

Rf CH$_3$CN/H$_2$O 85/15=0.47 on LKC18F (Whatman)

M.p.=110° C.

NMR (CDCl$_3$, 250 MHz) 7.00 (2H, m, H1 and H4); 6.93 and 6.63 (4H, 2d, AA'BB', aromatic H's in position 11); 6.82 (1H, dd, H2); 4.44 (1H, dd, J$_1$=55.5 Hz J$_2$=5 Hz, H17); 4.14 (2H, t, CH$_2$O); 4.03 (1H, m, H11); 3.35 (2H, t, CH$_2$I); 0.23 (3H, d, J=2 Hz, CH$_3$).

Stage C: Introduction of the Amine Followed by Deprotection.

0.4 ml of piperidine is added to a solution of the steroid prepared in the previous stage in 3 ml of THF, the reaction medium is taken to reflux for 2 hours then, after cooling down, poured into 10 ml of water, extracted with ethyl acetate, washed, dried and evaporated under reduced pressure in order to obtain 320 mg of the expected crude product. After dissolving in 30 ml of THF, 2 ml of tetrabutylammonium fluoride is added followed by heating at reflux for 7 hours. After cooling down, the reaction medium is poured into 20 ml of water saturated with sodium bicarbonate, extracted with ethyl acetate, washed, dried and evaporated under reduced pressure. 405 mg of crude product is obtained which is purified by chromatography on silica gel, eluting with an AcOET/TEA mixture 95/5. 160 mg of expected pure product is obtained.

Rf AcOEt/TEA 95/5 0.31 on $SiO_2F_{254}$ Merck.

NMR ($CDCl_3$ 300 MHz) 6.95 and 6.48(4H, 2d, AA'BB', aromatic H's in position 11); 6.79 (1H, d, H1); 6.48 (1H, d, H4); 6.39 (1H, dd, H2); 4.44 (1H, dd, J=56 Hz and 5 Hz, H17); 3.99 (1H, bt, H11); 4.26 and 3.99 (2H, 2m, $CH_2O$), 1.65 and 1.46 (6H, m, $CH_2$ in γ and β positions of the piperidine); 1.20 to 3.20 (20H, m skeleton H+$CH_2$N and $CH_2$ in αposition of the piperidine); 0.22 (3H, d, J=2 Hz, $CH_3$).

IR ($CHCl_3$)

OH 3597 $cm^{-1}$+associated

Aromatics 1608, 1582, 1512, 1503 $cm^{-1}$

EXAMPLE 2

17 alpha-fluoro-11-beta-[4-[2-(1-piperidinyl)ethoxy]phenyl]-estra-1,3,5(10)-trien-3-ol hydrochloride 2 ml of a 4N solution of HCl in ethyl acetate is added to a solution of the fluoridated compound of Example 1 in 10 ml of ethyl acetate at 0 +5° C., and crystallization is observed. 1.6 g of white crystals is obtained.

Rf AcOEt/TEA 95/5=0.21 on $SiO_2F_{254}$ Merck.

M.p.=216° C.

NMR ($CDCl_3$ 300 MHz) 6.95 and 6.43(4H, 2d, AA'BB', aromatic H's in position 11); 6.79(1H, d, H1); 6.66 (1H, d, H4); 6.59(1H, dd, H2) 4.43 (1H, dd, J=56 Hz and 5 Hz, H17); 3.99(1H, bt, H11); 4.26 and 3.87 (2H, 2m, $CH_2O$); 3.48(mobile 1H, $NH^+$); 2.8 to 3.25 (2H, m, $CH_2N^+$); 0.22 (3H, d, J=2 Hz, $CH_3$).

IR ($CHCl_3$)

OH 3598 $cm^{+1}$+associated $NH^+$ absorption aromatics 1610, 1582, 1512$cm^{-1}$

EXAMPLE 3

17 alpha fluoro-11 beta-[4-[2-(1-diethylamino)ethoxy]phenyl]-estra-1,3,5(10)-trien-3-ol The operation is carried out as in Example 1 but by using diethylamine instead of piperidine during Stage C, 0.141 g of expected product is obtained.

Rf AcOEt/Et3N 99/1=0.15 on $SiO_2F_{254}$ Merck.

NMR ($CDCl_3$ 300 MHz) 0.24 (d, $CH_3$ in position 18); 1.05 (t, C$\underline{H}_3$C$H_2$N); 2.64 (q, $CH_3$CH$\underline{H}$hd 2N); 2.83 (t, O—$CH_2$—C$\underline{H}_2$N); 3.95 (t, $CH_2O$); 4.00 (bt, H11); 4.44 (dd, J=56 Hz and 5 Hz, H17); 6.32 (d,$H_1$), 6.38 (dd, H2); 6.53 (d, H4); 6.57 and 6.96 (AA'BB", aromatic H's in position 11);

EXAMPLE 4

17 alpha-fluoro-11 beta-[4-[2-(1-pyrrolidinyl)ethoxy]phenyl]-estra-1,3,5(10)-trien-3-ol The operation is carried out as in Example 1 but by using pyrrolidine instead of piperidine during Stage C. 0.049 g of expected product is obtained.

Rf AcOEt/$ET_3$N 95/5=0.18 on $SiO_2F_{254}$ Merck.

NMR ($CDCl_3$ 300 MHz) 0.28(d, $CH_3$ in position 18); 2.70 (m, pyrroidine); 3.03 (t, $CH_2$N); 3.98 (t, $CH_2O$); 4.45 (dd, H17): 6.37 (dd, H2); 6.41 (d, H4); 6.50 and 6.96 (AA'BB', aromatic H's in position 11); 6.78 (d, H1)

EXAMPLE 5

4-chloro-17 alpha-fluoro-11-beta-[4-[2-(1-piperidinyl)ethoxy]phenyl]-estra-1,3,5(10)-trien-3-ol Stage A: Protection of 3-hydroxy 4-chloro-3-[[dimethyl(2,2-dimethyl)ethyl)silyl]oxy]-11 beta-[4-[2-(1-piperidinyl)ethoxy]phenyl]-estra-1,3,5(10)-trien-3-one 1.3 g of t-butyldimethylsilyl chloride is added to a solution of 4-chloro-3-hydroxy-11 beta-[4-[2-(1-piperidinyl)ethoxy]phenyl]-estra-1,3,5,(10)-trien-3-one prepared by the action of NCS on the corresponding Δ 4–5 9–10, 3-one derivative, followed by an aromatization reaction of the A ring in 30 ml of $CH_2Cl_2$, the reaction mixture is cooled down to 0° C. then 1.13 ml of TEA is added dropwise. After 5 minutes at 0° C., the reaction mixture is brought to ambient temperature and maintained for 3 hours followed by pouring into 100 ml of water.

After drying, the organic phase is evaporated off under reduced pressure in order to obtain 4.55 g of crude product, which is purified by chromatography on silica gel, eluting with an AcOEt/TEA mixture 98/2. 2.68 g of expected pure product is obtained.

Rf AcOEt/TEA 90/10=0.58 on $SiO_2F_{254}$ Merck.

IR ($CHCl_3$)

C=O 1733 $cm^{-1}$ aromatic C—H 2936–2859 $cm^{-1}$

Stage B: Reduction 4-chloro-3-[[dimethyl-(2,2-dimethylethyl)silyl)oxy)-11beta-[4-[2-(1-piperidinyl)ethoxy]phenyl]-estra-1,3,5(10)-trien-17 beta-ol 189 mg of $NaBH_4$ is added to a solution of the steroid obtained in the previous stage in 15 ml of methanol cooled down in an ice bath, followed by agitation for 5 minutes at 0+5° C. then for 30 minutes at ambient temperature. The reaction mixture is poured into 100 ml of water followed by extraction with ethyl acetate, washing, drying and evaporation under reduced pressure. 1.5 g of expected product is obtained.

Rf AcOEt/TEA 90/10=0.40 on $SiO_2F_{254}$ Merck.

Stage C: Fluoridation then Deprotection

Fluoridation 0.90 ml of DBU, 0.04 ml of perfluorobutane sulphonyl fluoride are added under nitrogen and at ambient temperature to a solution of 596 mg of the steroid obtained in the previous stage in 5 ml of toluene and 1 ml of $CH_2Cl_2$ and the reaction mixture is agitated for 2 hours. After pouring into 20 ml of water, extraction is carried out with dichloromethane followed by washing, drying and evaporation under reduced pressure. 1.23 g of crude product is obtained which is purified by chromatography on silica gel, eluting with an AcOEt/TEA mixture 98/2. 0.6 g of the fluoridated product protected in position 3 is isolated.

Deprotection 2 ml of $Bu_4NF$ is added to a solution of the fluoridated product in 3 ml of THF, followed by heating at reflux for 4 hours, then, after cooling down, pouring into 20 ml of water. After extraction with dichloromethane, washing and drying, evaporation is carried out under reduced pressure until a dry extract is obtained, which is purified by chromatography on Lichrosorb RP18, eluting with an MeOH/$H_2$O/TEA mixture 90/9/1. 65 mg of expected product is obtained.

Rf MeOH $H_2O$/TEA 90/9/1=0.23 on LKC18F (Whatman)

NMR ($CDCl_3$ 300 MHZ) 6.91 and 6.61 (4H, 2d, aromatic H in position 11); 6.80 (1H, d, H1); 6.61 (1H, d, H2); 4.34 (1H, dd, J=5 Hz and 55.5 Hz, H17); 3.98 (1H, masked, H11); 3.98 (2H, t, $CH_2O$); 2.70 (2H, t, $CH_2N$); 2.47 (4H, m, 2$CH_2$ in α position of the nitrogen of the piperidine); 1.58 (4H, m, $2CH_2$ in β position of the nitrogen of the piperidine); 1.44 (2H, m, $1CH_2$ in γ position of the nitrogen of the piperidine); 0.22 (3H, d, J=2.5 Hz, 18-Me).
IR ($CHCl_3$)
OH 3537 $cm^{-1}$
Aromatic 1608, 1581, 1512 $cm^{-1}$
By operating as in the previous examples, the following products were prepared:

EXAMPLE 6

17-iodo-11beta-[4-[2-(1-piperidinyl)ethoxy]-phenyl]-estra-1,3,5(10),16-tetraen-3-ol Rf: 0.33 (AcOEt-TEA 90-10).
IR ($CHCl_3$)
OH: 3600 $cm^{-1}$; aromatic: 1609, 1580, 1512 $cm^{-1}$.
NMR ($CDCl_3$, 300 MHz) 0.46: (s, $CH_3$ in position 18); 3.95: (m, $CH_2O$ and $H_{11}$); 6.11: ($H_{16}$); 6.36: (dd, $H_2$); 6.44: (d,$H_4$); 6.71: (d, $H_1$); ≈6.50–≈6.94: (aromatic in position 11).

EXAMPLE 7

17alpha-fluoro-11beta-[4-[2-(4-methyl-1-piperidinyl)ethoxy]-phenyl]-estra-1,3,5(10)-trien-3-ol Rf: 0.22 (AcOEt-TEA 99-1).
IR ($CHCl_3$)
OH: 3599 $cm^{-1}$; aromatic: 1610, 1581, 1512 (F) $cm^{-1}$.
NMR ($CDCl_3$, 300 MHz) 0.26: (s, $CH_3$ in position 18); 0.90: (d, $CH_3$ in position 4 of piperidinyl); ≈3.97: (m, $CH_2O$ and $H_{11}$); 4.43: (dd, $H_{17}$); 6.38: (dd, $H_2$); 6.46: (d, $H_4$); 6.80: (d, $H_1$); ≈6.50–≈6.95: (aromatic in position 11).

EXAMPLE 8

17alpha-fluoro-11beta-[4-[2-(4-methyl-1-piperidinyl)ethoxy]-phenyl]-estra-1,3,5(10)-trien-3-ol hydrochloride M.p. =200° C.
Rf: 0.15 (AcOEt-TEA 99-1).
NMR (DMSO, 300 MHz) 0.16: (s, $CH_3$ in position 18); 0.90: (d, $CH_3$ of in position 4 piperidinyl); 3.98: (bs, $H_{11}$); 4.25: (bs, $CH_2O$); 4.45: (dd, $H_{17}$); 6.31: (dd, $H_2$); 6.48: (d, J=2 $H_4$); 6.71: (d, $H_1$) 6.71–7.02: (aromatic in position 11); 8.97 (s, OH in position 3).

EXAMPLE 9

17alpha-fluoro-3-methoxy-11beta-[4-[2-(1-piperidinyl)ethoxy]-phenyl]-estra-1,3,5(10)-triene Rf: 0.23 (MeOH-$H_2O$-TEA 94-5-1).
IR ($CHCl_3$)
absence of OH; aromatic: 1610, 1578, 1512 1501 $cm^{-1}$.
NMR ($CDCl_3$, 300 MHz) 0.22: (s, $CH_3$ in position 18); 1.58: (m) and 2.47 (m): piperidine; 2.70: (t, $CH_2$—N): 3.73: (s, $CH_3$—O); 3.98: (t, $CH_2O$) ; 4.43: (dd, H17) ; 6.50: (dd, $H_2$); 6.64: (bs, $H_4$) ; 6.88: (d, $H_1$); ≈6.62–≈6.97: (aromatic in position 11).

EXAMPLE 10

17alpha-fluoro-3-methoxy-11beta-[4-[2-(1-pyrrolidinyl)ethoxy]-phenyl]-estra-1,3,5(10)-triene M.p.=132° C.
Rf: 0.21 (MeOH-$H_2O$-TEA 94-5-1).
IR ($CHCl_3$)
aromatic: 1610, 1578, 1512 1501 $cm^{-1}$.
NMR ($CDCl_3$, 300 MHz) 0.22: (s, $CH_3$ in position 18); 1.78: (m) and 2.58 (m): pyrrolidine; 2.83: (t, $CH_2$—N): 3.73: (s, $CH_3$—O) ; 3.99: (t, $CH_2O$); 4.43: (dd, H17); 6.50: (dd, $H_2$); ≈6.65: (H4); 6.89: (d, $H_1$); ≈6.64–≈6.97: (aromatic in position 11).

EXAMPLE 11

17alpha-fluoro-3-methoxy-11beta-[4-[2-(diethylamino)ethoxy]-phenyl]-estra-1,3,5(10)-triene Rf: 0.20 (MeOH-$H_2O$-TEA 94-5-1).
IR ($CHCl_3$)
aromatic: 1610, 1578, 1512 1501 $cm^{-1}$.
NMR ($CDCl_3$, 300 MHz) 0.22: (s, $CH_3$ in position 18); 1.04: (t) and 2.61 (q): N-$Et_2$; 2.82: (t, $CH_2$—N): 3.73: (s, $CH_3$—O) ; 3.94: (t, $CH_2O$); 4.43: (dd, $H_{17}$); 6.49: (dd, $H_2$); 6.64: (d, $H_4$); 6.88: (d, $H_1$); ≈6.62–≈6.96: (aromatic in position 11).

EXAMPLE 12

(11beta)-17-chloro-11-[4-[2-(1-piperidinyl)ethoxy]-phenyl]-estra-1,3,5(10), 16-tetraen-3-ol Rf: 0.25 ($CH_2Cl_2$-MeOH-$NH_4OH$ 95-5-0.5).
NMR ($CDCl_3$, 300 MHz) 0.60: (s, $CH_3$ in position 18); ≈4.01: (m, $CH_2O$ and $H_{11}$); 5.60: (bd, $H_{16}$); 6.38: (dd, $H_2$); 6.45: (d, $H_4$); 6.70: (d, $H_1$); ≈6.50–≈6.93: (aromatic in position 11).

EXAMPLE 13

17alpha-chloro-11beta-[4-[2-(1-piperidinyl)ethoxy]-phenyl]-estra-1,3,5(10)-trien-3-ol Rf: 0.10 ($CH_2Cl_2$-MeOH-$NH_4OH$ 94-5-0.1).
NMR ($CDCl_3$, 300 MHz) 0.41: (s, $CH_3$ in position 18); ≈3.98: (m, $CH_2O$ and $H_{11}$ and $H_{17}$); 6.39: (dd, $H_2$); 6.48: ($H_4$); 6.79: (d, $H_1$); ≈6.48–≠6.94: (aromatic in position 11).

EXAMPLE 14

17iodo-11beta-[4-[2-(1-piperidinyl)ethoxy]-phenyl]-estra-1,3,5(10),16-tetraen-3-ol hydrochloride M.p.=260° C.
Rf: 0.33 (AcOEt-TEA 90-10).
NMR (DMSO, 300 MHz) 0.29: (s, $CH_3$ in position 18); 4.02: (bt, $H_{11}$); 4.25: (bs, $CH_2O$); 6.15: (bs, $H_{16}$); 6.29: (dd, $H_2$); 6.48: (d, $H_4$); 6.64: (d, $H_1$); ≈6.73–≈7.01: (aromatic in position 11); 8.94–≈9.78: mobile H's.

EXAMPLE 15

17alpha-fluoro-11beta-[4-[2-(1-piperidinyl)ethoxy]-phenyl]-estra-1,3,5(10)-trien-3-ol lactate M.p.=138° C.
NMR ($CDCl_3$, 300 MHz) 0.22: (d, $CH_3$ in position 18); ≈3.15; ($CH_2N$); ≈3.94: (m, $CH_2$—O); ≈3.98: (m, $H_{11}$); 4.43: (dd, $H_{17}$); 6.42: (dd, H2); 6.78: (d, $H_1$); ≈6.48–≈6.97: (aromatic in position 11); 1.36 (d) and 4.09 (m): lactate.

Pharmacological Tests
Effect on the Proliferation of Mammary Cells
The proliferative activity of the molecules is studied in comparison to that of oestradiol on MCF-7 human mammary cells in culture.

In order to demonstrate an agonist effect of the oestradiol and/or the tested molecules, the cell maintenance culture medium (rich in growth factors and steroids) is replaced by an impoverished medium, inter alia free of steroids (DMEM supplemented with 5% of steroid-free serum and without phenol red). Cells undergo this severance two days before the start of the test.

After 7 days culture in the presence of the products to be studied, the cell proliferation is evaluated by determination of the DNA. In each test, the effect of the oestradiol at $10^{-10}$M (cell growth in the presence of oestradiol less cell growth in the presence of the solvent) determines the 100% agonist activity. The activity of the molecules is evaluated in comparison to this internal control. The molecules inducing an identical cell growth to that observed with the solvent alone are classified as "inactive", those inducing a lower cell growth to that observed with the solvent are classified as "inhibitor".

| | ACTIVITY |
|---|---|
| Oestradiol | Agonist |
| Example 1 | Inactive |
| Example 2 | Inactive |

Bone impact study of a product in the ovariectomized female rat at the age of 3 months The compounds are tested in order to determine their effect on the bone mass and on the formation and resorption activity in the model of the ovariectomized rat at the age of 3 months. The animals are treated in a preventive fashion.

| Animals: | |
|---|---|
| Species | rat |
| Strain | Sprague-Dawley |
| Sex | female |
| Weight | 250 g to 230 g |
| No. of animals/group | 8 |

Products:
1—Product to be tested: Product of Example 1.
  vehicle(s): corn oil, 0.5% methylcellulose
  number of administrations: once/day; 5 days/week for 4 weeks
  administration route: oral route for the product
  volumes: 5 ml/kg (p.o.)
  period between the last injection and sacrifice: 24 hours
  number of administrations: 20.
2—Reference product: 17β oestradiol is administered by subcutaneous route at a dose of 0.1 or 0.01 mg/kg/d in solution in a mixture of corn oil-benzyl alcohol (99:1, v/v) under a volume of 0.2 ml/kg.

Experimental Protocol

Animals

The study is carried out with female rats ovariectomized at the age of 3 months. The animals are kept in an air-conditioned room (temperature 20° C.±2° C.) and grouped by 4 into boxes. The animals receive, ad libitum, demineralized water and compressed foods (pellets: AO4CR-10 UAR).

Surgery

The 3 month old female rats weighing approximately 250 g are ovariectomized under anaesthesia with Imalgene 1000, at a dose of 100 mg/kg by intraperitoneal route (i.p.) and under a volume of 1 ml/kg. They also receive Nembutal (3 mg/kg i.p. under a volume of 0.3 ml/kg).

After lateral incision, the cutaneous and muscular planes are sectioned. The exeresis of each ovary is carried out after ligature of the oviduct.

The "SHAM" control rats are anaesthetised under the same conditions. After incision of the cutaneous and muscular planes, each ovary is exposed then replaced in situ.

Treatment

The effects of the products are determined in a preventive treatment. They are administered immediately after the ovariectomy. Animals are distributed into groups of 8.

Group 1: "SHAM" control rats receiving the vehicle or vehicles.

Group 2: "OVX" control rats receiving the vehicle or vehicles.

Groups X: "OVX" rats receiving respectively defined doses of the product or products to be tested.

Blood Samples

At the end of 4 weeks (duration of the study) the animals are decapitated by guillotine. The serums collected after centrifugation are preserved at −20° C.

A lipidic balance will be established from the serous determinations of total cholesterol, of triglycerides and of phospholipids on a 500 μl aliquot of serum. Lowering of the serous cholesterol level is expressed in % relative to the level shown by the ovariectomized animals receiving only the solvent.

Organ Samples

After sacrificing the animals, the following organs are removed:

tractus genitalis

The uteri are removed. The latter are weighed. The increase in weight is expressed in % of the weight of the uterus of ovariectomized animals receiving only the solvent.

at the bone level:

The bone mass (BMD or bone mineral density) is measured by biphotonic dual energy X-ray absorptiometry (DEXA). The measurements are carried out on bone excized and cleaned of all soft tissue. The BMD (bone mineral density) is measured on the whole bone as well as on the metaphyseal part at the level of the proximal extremity for the left tibia. This zone is defined as being the region which is richest in trabecular bone; and consequently, is the most sensitive to variations in bone volume and bone mineral density.

The results are expressed in % according to the formula:

$$\frac{\text{Tested product BMD} - \text{OVX BMD}}{\text{SHAM BMD} - \text{OVX BMD}} \times 100$$

| | Dose Route mg/kg | TIBIA BONE BMD % | UTERUS Weight % | Cholesterol % |
|---|---|---|---|---|
| OVX | | 0 | | |
| SHAM | | 100 | | |
| Oestradiol | 0.1 s.c. | 139 | 220 | −3 |
| Ex. 1 | 0.3 po | 73 | 41 | −51 |
| Oestradiol | 0.01 s.c | 95 | 317 | −16 |
| Ex. 1 | 0.1 po | 57 | 67 | −49 |
| | 0.3 po | 71 | 70 | −59 |
| | 1.0 po | 72 | 93 | −61 |

What is claimed is:

1. A compound selected from the group consisting of a compound of the formula

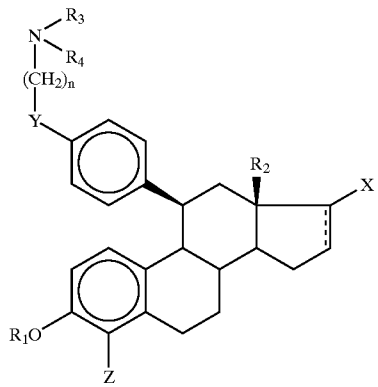

I wherein $R_1$ is selected from the group consisting of hydrogen, —$(CH_2)_m$—Ar, —(CO)—Ar, —$(CH_2)_m$—Alk and —(CO)—Alk, $R_2$ is unsaturated or saturated hydrocarbon of up to 6 carbon atoms, X is halogen, Y is selected from the group consisting of —O—, —S—, —NH—, —SO—, —$SO_2$— and a single bond, Z is hydrogen or halogen, n is an integer from 2 to 5, $R_3$ and $R_4$ are individually selected from the group consisting of hydrogen, —$(CH_2)_{m'}$—Ar, —$(CH_2)_{m'}$—Het and —$(CH_2)_{m'}$—Alk or taken together with the nitrogen to which they are attached form an unsaturated or saturated, aromatic or non-aromatic mono- or polycyclic heterocycle of 3 to 15 members optionally containing 1 to 3 additional heteroatoms selected from the group consisting of oxygen, sulfur and nitrogen unsubstituted or substituted, Ar is a carbocyclic aryl of 6 to 18 carbon atoms, Het is unsaturated or saturated, aromatic or non-aromatic heterocycle of 1 to 9 carbon atoms and 1 to 5 heteroatoms selected from the group consisting of oxygen, sulfur and nitrogen, Alk is saturated or unsaturated alkyl or cycloalkyl of up to 12 carbon atoms, m and m' are integers from 0 to 3, the dotted line indicates a possible second bond, the Ar, Het and Alk being unsubstituted or substituted with at least one member of the group consisting of halogen, alkoxy, alkylthio, —$NH_2$, mono- and dialkylamino optionally oxidized, aminoalkyl, dialkylaminoalkyl, —OH, acyloxy, acyl, carboxy, alkoxy carbonyl, —CN, —$CF_3$, aryl, aralkyl and alkyl, alkenyl and alkyl unsubstituted or substituted by a member of the group consisting of halogen, alkyl, alkoxy, alkylthio, —$NH_2$ and mono- and dialkylamino and its non-toxic, pharmaceutically acceptable acid and base salts.

2. A compound of claim 1 wherein X is α-fluorine and the dotted line is not a second bond.

3. A compound of claim 1 wherein $R_1$ is hydrogen, $R_2$ is methyl, Z is hydrogen or chlorine, Y is oxygen and the dotted line is not a second bond.

4. A compound of claim 1 wherein $R_3$ and $R_4$ are individually alkyl of 1 to 6 carbon atoms or taken with the nitrogen form a member of the group consisting of

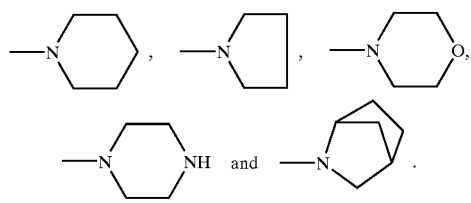

5. A compound of claim 1 wherein X is α-fluorine, $R_1$ is hydrogen, $R_2$ is methyl, Y is oxygen, Z is hydrogen or chlorine, n is 2 or 3, $R_3$ and $R_4$ are individually alkyl of 1 to 6 carbon atoms or taken together with the nitrogen form a member selected from the group consisting of

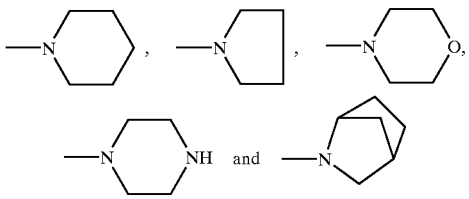

6. A compound of claim 1 selected from the group consisting of:

17-alpha-fluoro-11-beta-[4-[2-(1-piperidinyl)ethoxy] phenyl]-estra-1,3,5(10)-trien-3-ol 17-alpha-fluoro-11-beta-[4-[2-(1-piperidinyl)ethoxy] phenyl]-estra-1,3,5(10)-trien-3-ol hydrochloride 17-alpha-fluoro-11-beta-[4-[2-(1-diethylamino)ethoxy] phenyl]-estra-1,3,5(10)-trien-3-ol 17-alpha-fluoro-11-beta-[4-[2-(1-pyrrolidinyl)ethoxy] phenyl]-estra-1,3,5(10)-trien-3-ol 4-chloro-17-alpha-fluoro-11-beta-[4-[2-(1-piperidinyl) ethoxy]phenyl]-estra-1,3,5(10)-trien-3-ol 17-iodo-11-beta-[4-[2-(1-piperidinyl)ethoxy]phenyl]-estra-1,3,5(10),16-tetraen-3-ol, 17-alpha-fluoro-11-beta-[4-[2-(4-methyl-1-piperidinyl) ethoxy]-phenyl]-estra-1,3,5(10)-trien-3-ol, 17-alpha-fluoro-11-beta-[4-[2-(4-methyl-1-piperidinyl) ethoxy]-phenyl]-estra-1,3,5(10)-trien-3-ol hydrochloride, 17-alpha-fluoro-3-methoxy-11-beta-[4-[2-(1-piperidinyl) ethoxy]-phenyl]-estra-1,3,5(10)-triene, 17-alpha-fluoro-3-methoxy-11-beta-[4-[2-(1-pyrrolidinyl) ethoxy]-phenyl]-estra-1,3,5(10)-triene, 17-alpha-fluoro-3-methoxy-1-beta-[4-[2-(diethylamino) ethoxy]-phenyl]-estra-1,3,5(10)-triene, (11-beta)-17-chloro-11-[4-[2-(1-piperidinyl)ethoxy]- phenyl]-estra-1,3,5(10),16-tetraen-3-ol, 17-alpha-chloro-11-beta-[4-[2-(1-piperidinyl)ethoxy]- phenyl]-estra-1,3,5(10)-trien-3-ol, 17-iodo-11beta-[4-[2-(1-piperidinyl)ethoxy]-phenyl]-estra-1,3,5(10),16-tetraen-3-ol hydrochloride, 17-alpha-fluoro-11beta-(4-(2-(1-piperidinyl)ethoxy]-phenyl]-estra-1,3,5(10)-trien-3-ol.

7. A composition for hormone replacement therapy in menopause or perimenopause comprising an effective amount of a compound of claim 1 sufficient for hormone replacement and an inert pharmaceutical carrier.

8. A method of hormone replacement for treating menopause or perimenopause without activity at the uterine level in warm-blooded female animals in need thereof comprising administering to warm-blooded female animals an amount of a compound of claim 1 sufficient for hormone replacement without activity at the uterine level.

9. A method of treating osteoporosis in warm-blooded animals comprising administering to warm-blooded animals in need thereof an amount of a compound of claim 1 sufficient to treat osteoporosis.

10. A method of strengthening cardiovascular protection in warm-blooded animals comprising administering to warm-blooded animals in need thereof an amount of a compound of claim 1 sufficient to strengthen cardiovascular protection.

* * * * *